(12) United States Patent
Schoch et al.

(10) Patent No.: US 11,378,299 B2
(45) Date of Patent: Jul. 5, 2022

(54) METADATA DRIVEN METHOD AND SYSTEM FOR AIRBORNE VIRAL INFECTION RISK AND AIR QUALITY ANALYSIS FROM NETWORKED AIR QUALITY SENSORS

(71) Applicant: MANN+HUMMEL LIFE SCIENCES & ENVIRONMENT HOLDING SINGAPORE PTE. LTD., Singapore (SG)

(72) Inventors: Marcel Schoch, Ludwigsburg (DE); Michael Shanahan, Chula Vista, CA (US); Elham Amirnasr, Durham, NC (US)

(73) Assignee: MANN+HUMMEL GmbH, Ludwigsburg (DE)

( * ) Notice: Subject to any disclaimer, the term of this patent is extended or adjusted under 35 U.S.C. 154(b) by 87 days.

(21) Appl. No.: 17/088,826

(22) Filed: Nov. 4, 2020

(65) Prior Publication Data

US 2022/0136730 A1    May 5, 2022

(51) Int. Cl.

| | | |
|---|---|---|
| *F24F 11/89* | (2018.01) | |
| *F24F 11/48* | (2018.01) | |
| *F24F 11/49* | (2018.01) | |
| *F24F 11/32* | (2018.01) | |
| *G16H 50/80* | (2018.01) | |

(52) U.S. Cl.
CPC .............. *F24F 11/89* (2018.01); *F24F 11/32* (2018.01); *F24F 11/48* (2018.01); *F24F 11/49* (2018.01); *G16H 50/80* (2018.01)

(58) Field of Classification Search
CPC .. F24F 11/89; F24F 11/32; F24F 11/48; F24F 11/49
See application file for complete search history.

(56) References Cited

U.S. PATENT DOCUMENTS

| | | |
|---|---|---|
| 10,767,879 B1 | 9/2020 | Burnett |
| 10,775,068 B2 | 9/2020 | Lee et al. |
| 2013/0031011 A1* | 1/2013 | Lee ................. G06Q 30/02 705/306 |
| 2020/0124580 A1 | 4/2020 | Wallis |
| 2020/0200416 A1* | 6/2020 | Granger ............. F24F 11/30 |
| 2020/0317368 A1 | 10/2020 | Sunstrand |
| 2021/0375440 A1* | 12/2021 | Schlameuss ......... G05B 15/02 |
| 2021/0390812 A1* | 12/2021 | Chaurasia ............ G07C 9/27 |
| 2021/0391089 A1* | 12/2021 | Eswara ............. G16H 50/80 |
| 2021/0398690 A1* | 12/2021 | Gibson ............. G16H 50/80 |
| 2022/0042694 A1* | 2/2022 | He .................. F24F 11/88 |
| 2022/0067851 A1* | 3/2022 | Sinha .............. G06F 3/0482 |

\* cited by examiner

*Primary Examiner* — Ronald D Hartman, Jr.

(57) ABSTRACT

A computer implemented system and process of analyzing real-time measurements of a plurality of air quality sensors to provide an calculated estimate of airborne virus infection and air quality evaluation from current air quality measurements, advise those at risk, advise responsible parties of recommended actions to take, and in some embodiments take direct action in communication of instructions to air filtration and treatment equipment and HVAC systems to improve outside air flow, increase filtration, treat contaminated air and reduce humidity and reduce the risk of airborne virus transmission. Sensor data, calculated airborne infection risk, air quality, warnings and reports are created and distributed to network connected devices.

5 Claims, 5 Drawing Sheets
(3 of 5 Drawing Sheet(s) Filed in Color)

METADATA DRIVEN METHOD AND SYSTEM FOR AIRBORNE VIRAL INFECTION RISK AND AIR QUALITY ANALYSIS FROM NETWORKED AIR QUALITY SENSORS

TECHNICAL FIELD

The subject matter described and disclosed herein relates to air quality monitoring of rooms or spaced in buildings, and more particularly to networked analysis systems and method interacting continuously or periodically with a plurality of remotely located networked air quality sensors, analyzing to assess the risk of airborne virus infection and air quality from sensor real-time air quality measurements. The subject matter further relates to reporting trends of risk factors, generation of alarms and actionable messages to managers, building owners and occupants regarding air quality and a calculated risk of airborne virus infection, particularly SARS-COV-2/COVID.

BACKGROUND OF THE INVENTION

Air quality is an important issue for decades. Today we have the increasing levels of pollution and climate change related forest fires. Even more critical to families and human life, health and our world economy is deaths and hospitalizations of the SARS-COV-2 pandemic. The future will hold new and unknown viral pandemics.

Various air quality monitoring devices and sensors are known. What is still lacking in the art is an autonomous computer implemented system and analysis method for analyzing real-time measurements of a plurality of networked air quality sensors in one or more monitored air spaces in one or more building, dispersed, and analyzing the measurements to determine a risk of airborne viral infection transmission. Such a system would fill an unmet need in the determination and reduction in the risk of airborne viral infection transmission to occupants in buildings, public spaces, schools, offices, shopping malls, and then facilitate their reopening and safe operation.

SUMMARY OF THE INVENTION

Coronaviruses such as SARS-COV-2 are well known to be spread from person to person. The virus most often spreads through people who have symptoms, but not always. Unfortunately it is possible to pass the virus on to other people even when the infected carrier shows no visible signs of being infected. People who don't know they've been infected can unintentionally infect others. This is called asymptomatic spread. There are several modes of transmission for this to happen.

Contact transmission—Surfaces may become contaminated with the virus when someone who has the virus touches, coughs or sneezes near or onto the surface. Virus containing droplets or micro droplets may settle onto surfaces, contaminating them. Prevention strategies include surface disinfectants and improved cleaning schedules.

Respiratory transmission—When an infected person coughs, sneezes, or talks, droplets from the infected person carry the virus into the air from their nose or mouth. Larger droplets may fall to the ground relatively quickly. For larger droplets, social distancing and PPE (personal protective equipment) such as face masks are known to be prevention strategies.

Airborne transmission—Social distancing and PPE are less effective or ineffective with airborne transmission of virus laden micro droplets. Airborne transmission of virus carrying micro droplets are available to infect persons entering a room, even if for an extended time long after the infected individual has left. Long distance transmission over a longer time via virus-laden micro droplets has been recorded, first on cruise ships, and then restaurants and shopping malls. Micro droplets can remain airborne for a longer period of time, for example 30 minutes or longer, and so are available to infect persons entering a room for significant time after the infected individual has left. Prevention strategies here include air quality monitoring (such as the method and system disclosed herein), ventilation, air filtration and purification.

An object of the present inventive disclosure is to provide a computer implemented system and method of analyzing real-time measurements of a plurality of air quality sensors to calculate an overall airborne virus infection risk score, to advise others at risk. In some embodiments of the invention, the computer implemented system and method of analyzing real-time measurements of a plurality of air quality sensors may be configured to take direction action by communicating set points and commands over the network to HVAC systems, or to portable air treatment/filtering appliances to improve outside air flow, increase filtration, reduce humidity, etc., improving room air quality and reducing viral infection risk. The real-time measurements of several air quality parameters have been correlated with the risk of indoor virus infection and so are useful, in combination, for calculating a risk of airborne virus risk infection from, for example, SARS-COV-2.

The computer disclosed method and system autonomously scans, detects, analyzes and informs of known critical pollutants, which add to airborne virus transmission, calculates the risk and provides actionable recommendations on how to minimize risk for building occupants. A SARS-CoV-2 Airborne Virus Infection Risk Score, (CAIRS) is introduced herein which spans numerically from 0 to 100 and splits or chunks the risk levels into three categories: Low (0-33), Moderate (34-66), and High (67-100) as a simplified presentation of risk.

For example, studies have shown that carbon dioxide ($CO_2$) is directly correlated with virus concentration in the air if an infected person is in the room. Therefore $CO_2$ concentration in the air is a great indicator for indoor infection risk determination.

Particulate matter (PM) in the air is useful as an indicator of filtration efficiency. Increased PM levels put additional stress on the human respiratory system, and are suspected to function as virus carriers. Measurement of PM 2.5 and PM 10 concentrations can be used as a proxy to determine aerosol concentrations.

Humidity is important. Corona viruses decays slower in dry and in very humid environments. Additionally too high of a humidity level may increase the risk for building damage.

A published study of "Effects of Air Temperature and Relative Humidity on Coronavirus Survival on Surfaces" as published by the American Society of Microbiology (Lisa M. Casanova et al.) found that the greatest level of virus inactivation took place at 50% RH. In the study, the lowest level of virus inactivation took place at 20% RH. Virus inactivation is more rapid at 20 C than at 4 C at all humidity levels. Viruses were inactivated more rapidly at 40 C than at 20 C. Interestingly, the relationship between inactivation and relative humidity (RH) was not monotonic. There was a greater virus survival or greater protective effect at low RH (20%) and high RH (80%) than at moderate RH (50%).

A study published by the National Center for Biotechnology Information, U.S. National Library of Medicine, titled: "Influence of airborne transmission of SARS-CoV-2 on COVID-19 pandemic. A review" and published online Jun. 23, 2020 found than an increase of only 1 microgram per cubic meter of air in PM2.5 is associated with an 8% increase in the SARS-COV-2 death rate. The results were statistically significant and robust to secondary and sensitivity analysis. A small increase in long term exposure to PM2.5 is linked to a large increase in SARS-COV-2 death rate The Sars-COV-2 pandemic is a devastating to human health in epic proportions, endangering individual well-being, family health and survival, and ultimately the world economy.

As can be seen from the above, there remains a significant need for a computer implemented cross network implemented process and system of gathering real-time air quality measurement of building rooms or enclosed spaces, and applying for continuous analyzing the measures to manage or control indoor air quality parameters to reduce the risk of airborne virus transmission and resulting infection. Such a system find value by meeting a significant human health need in monitoring indoor air quality and using this information to calculate a real-time virus infection risk score, monitoring indoor airspaces and altering building owners or occupants when conditions change, increasing risk, and by generating actionable alerts to responsible individuals or group for corrective actions, or in other cases direct output instructions to building HVAC control system, implementing changes to ventilation, filtration, humidity and air quality factors to effect the reduction in the risk of airborne virus transmission. Disclosing such a solution in a system and method is a primary objective of this inventive disclosure.

According to a first aspect of the invention disclosure, a computer implemented process or method is provided herein for interacting with, obtaining measurements from and analyzing real-time measurements of a plurality of air quality sensors arranged in monitored air spaces in one or more building and then calculating and sharing an infection risk score from the measured parameters. The computer-implemented process is executed on an infection risk analysis server computer that may be located at significant distances away from the monitored building(s) and the air quality sensors provided therein. Communication between the analysis system and the sensors occurs continuously/periodically and autonomously by data communication or packets over a wide area network such as the Internet.

Studies have shown that:

A greater level of virus inactivation occurs around at 50% RH.

A much lower level of virus inactivation occurs around 20% RH.

Virus inactivation occurs more rapidly at 20 C than 4 C at all humidity values.

Viruses were inactivated more rapidly at 40 C than 20 C.

However, the relationship not monotonic. Greater virus survival occurs at low RH 20% and high RH 80% than at moderate RH 50%.

Studies have shown that infectious corona virus deposited on stainless steel have persisted for at least 3 days at 50% RH &20 C and for up to 28 days at 20% RH.

In heated dry indoor air (20 C, 20% RH), 80% of corona viruses on surfaces have been shown to be viable for a week. Humidification of the air 50% RH reduces viable viruses to less than 1% in 20 days (fastest deactivation) and significantly decreases infection risk ($-2.5*\log_{10}$ in two days).

Virus Inactivation at 20% RH 20 C: Inactivation $\log_{10}=-0.081\%/day$

Virus Inactivation at 80% RH 20 C: Inactivation $\log_{10}=-2.12\%/day$

Virus Inactivation at 50% RH 20 C: Inactivation $\log_{10}=-0.896\%/day$

Studies have shown that an increase of 1 μgram/m$^3$ in PM2.5 has been associated with an 8% increase of SARS-COV-2 death rate.

As such, the computer implemented analysis system and method of the present disclosure provides significant benefit to human health and survival in the SARS-COV-2-19 pandemic and is very likely applicable to future coronavirus or viral pandemics.

In aspects of the invention, the present inventive disclosure provides a computer implemented system and method of analyzing real-time measurements of a plurality of network connected air quality sensors to calculate an Air Quality Index (AQI) for each of a plurality of indoor air spaces or rooms of one or more buildings. The computer implemented system and method performs this and the airborne virus risk infection for building that may be dispersed across great distances, such as differing continents, in different continents or countries, as the computer implemented system and method is specifically configure to interact with the air quality sensors autonomously through a wide area network.

The Air Quality Index (AQI) was created by the U.S. Environmental Protection Agency (EPA) and is determined by the worst relative pollutant concentration measured. Each category corresponds to a different level of health concern. The six levels of concern, according to the EPA, and what they entail are:

Good—AQI is 0 to 50. Air quality is considered satisfactory, and air pollution poses little or no risk.

Moderate—Air quality is acceptable; however, for some pollutants there may be moderate health concern for a very small number of people.

Unhealthy for Sensitive Groups—AQI is 101 to 150. Although the general public is not likely to be affected at this AQI range, persons with heart and lung disease, older adults, and children are at greater risk.

Unhealthy—AQI is 151 to 200. Everyone may begin to experience some adverse health effects, and members of the sensitive groups may experience more serious effects.

Very Unhealthy—AQI is 201 to 300. The air quality is dangerous and would trigger a health alert signifying that occupants may experience serious health complications.

Hazardous—AQI greater than 300. This would trigger a health warning of emergency conditions. The entire population is more likely to be affected.

Air pollutant sources and associated networked monitored air spaces sensors may include:

Particulate Matter (PM2.5, PM10). Common sources are Industry, traffic, cooking and indoor smoking. Health impacts include heart disease and cancer.

Volatile Organic Compounds (VOCs). Volatile organic compounds (VOCs) are organic chemicals that have a high vapor pressure at ordinary room temperature. Their high vapor pressure results from a low boiling point, which causes large numbers of molecules to evaporate from the liquid or solid form of the compound and enter into the surrounding air, a trait known as volatility. Common sources are paint, aerosols, cleansers, carpets, furniture. Health impacts include respiratory irritation, damage to liver and kidneys. Formaldehyde (HCHO) and other volatile organic compounds (VOCs), for example toluene and xylenes, are a concern due to their toxicity. Formaldehyde is a priority VOC because of its frequent occurrence in indoor air and the serious health outcomes resulting from exposure. Common sources include building materials, cleaners. Health impacts include irritation of the skin, eyes, nose, and throat.

Carbon Dioxide ($CO_2$)—Common sources include breathing, combustion of fossil fuels. Health impacts include headaches and fatigue.

In another aspect of the invention, the computer implemented system and method of analyzing real-time measurements of a plurality of network connected air quality sensors analyzes the sensor data and provides a real-time air quality overview to a sets of network connected devices configured to receive AQI updates for buildings, rooms, stores, conference rooms school rooms, etc. and trend the Air Quality Index (AQI) data time, providing graphs and reports to connected devices configured to receive AQI updates. Data is also accessible through a web portal provided by the computer implemented system, accessible from network connected smart phones, tablet, or device, accessible, for example, though web browsers.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying Figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
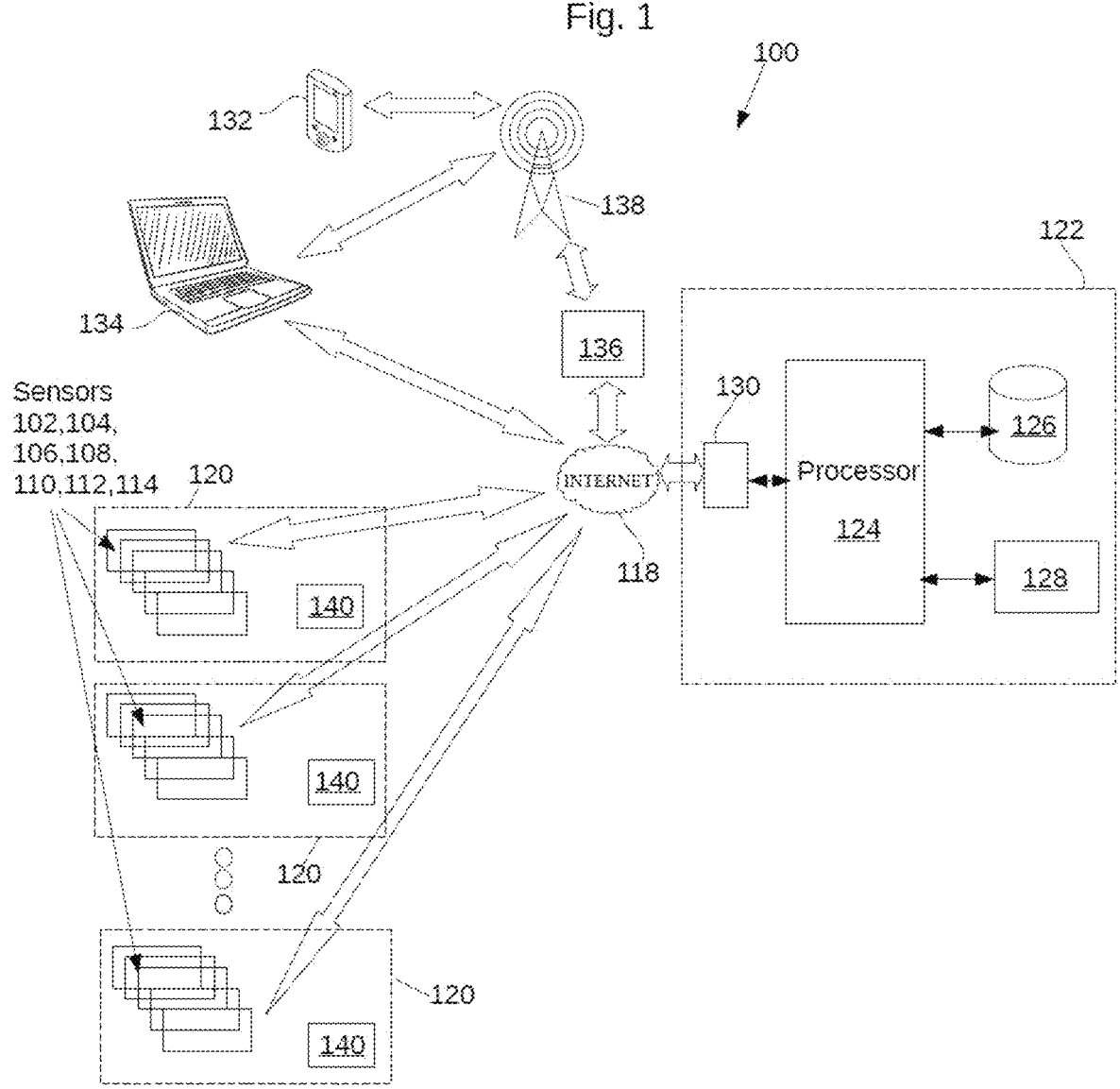

Features of the present invention, which are believed to be novel, are set forth in the drawings and more particularly in the appended claims. The invention, together with the further objects and advantages thereof, may be best understood with reference to the following description, taken in conjunction with the accompanying drawings. The drawings show a form of the invention that is presently preferred; however, the invention is not limited to the precise arrangement shown in the drawings.

Figure 2:
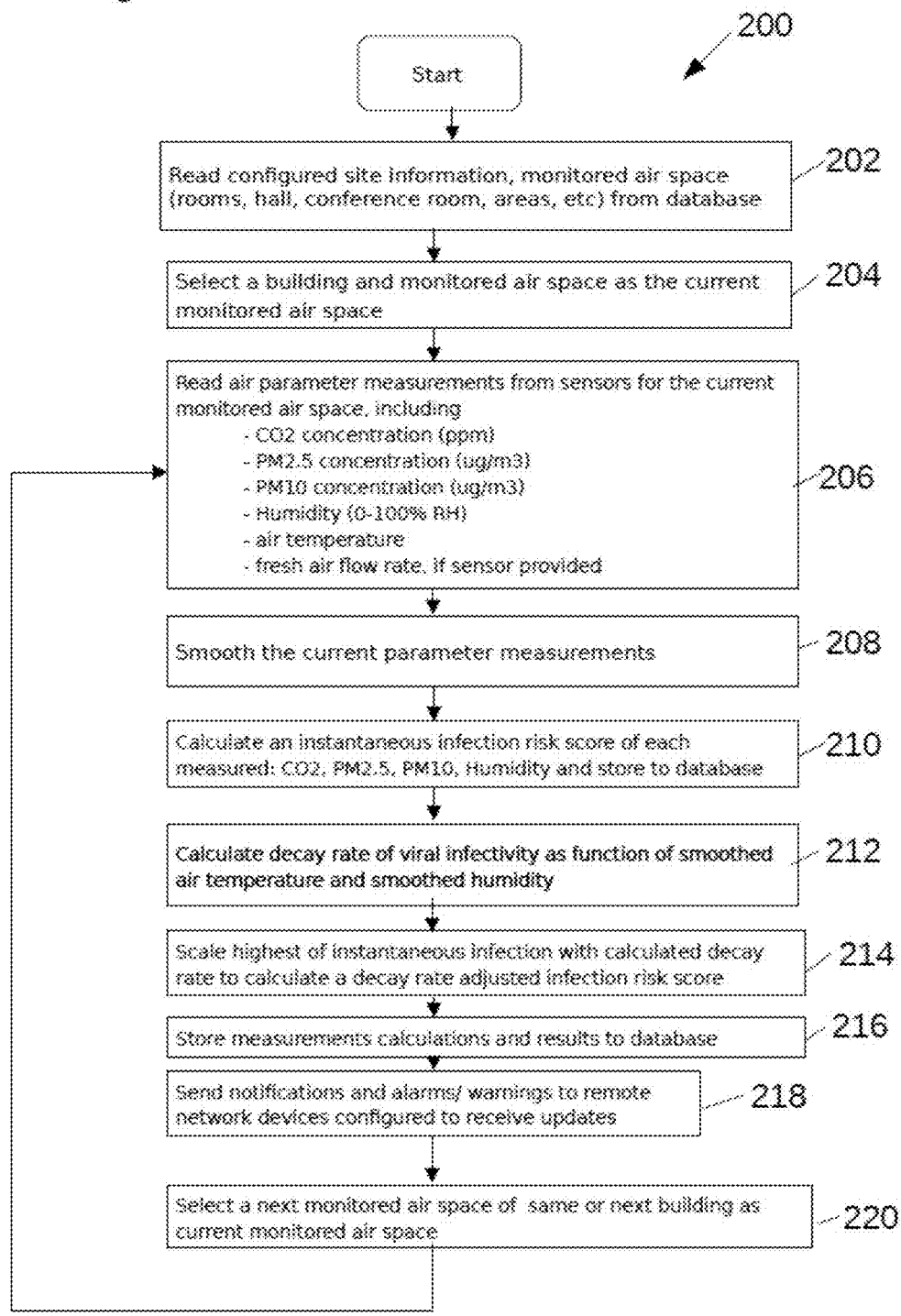
Figure 5:
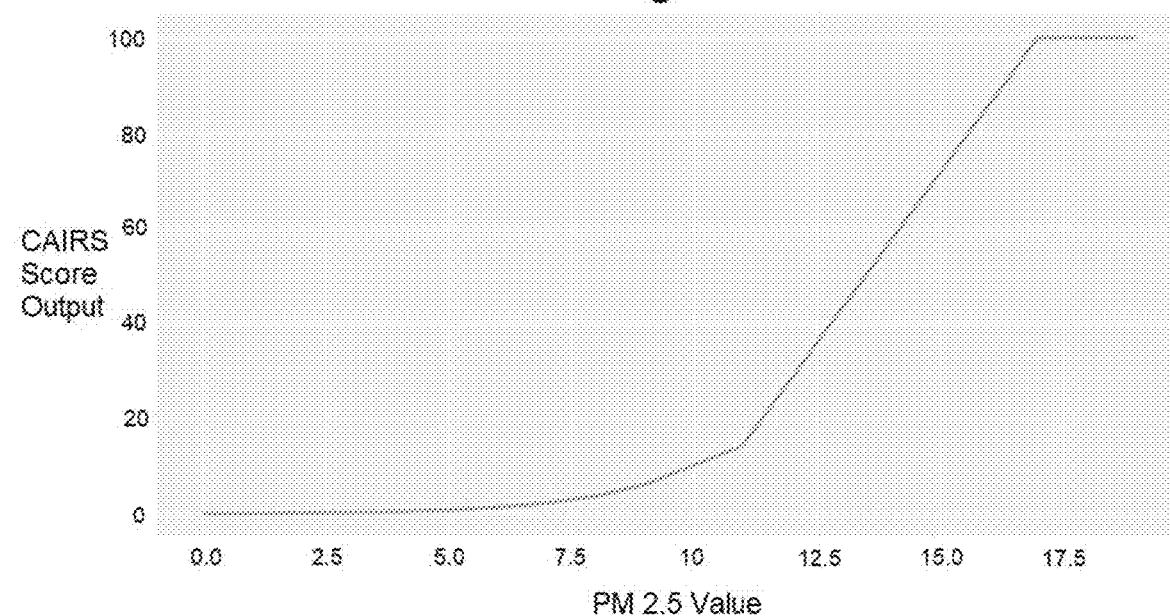
Figure 6:
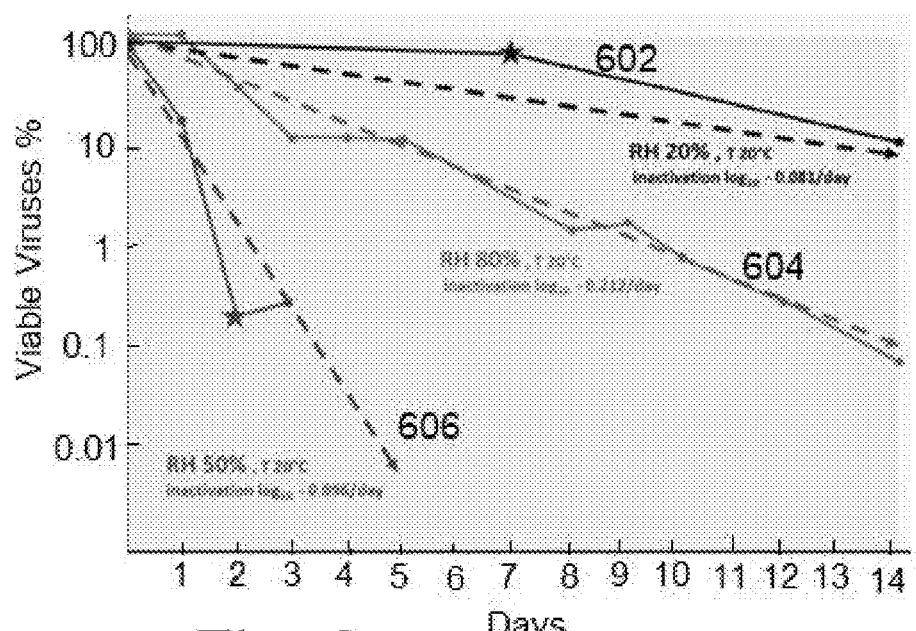
Figure 7:
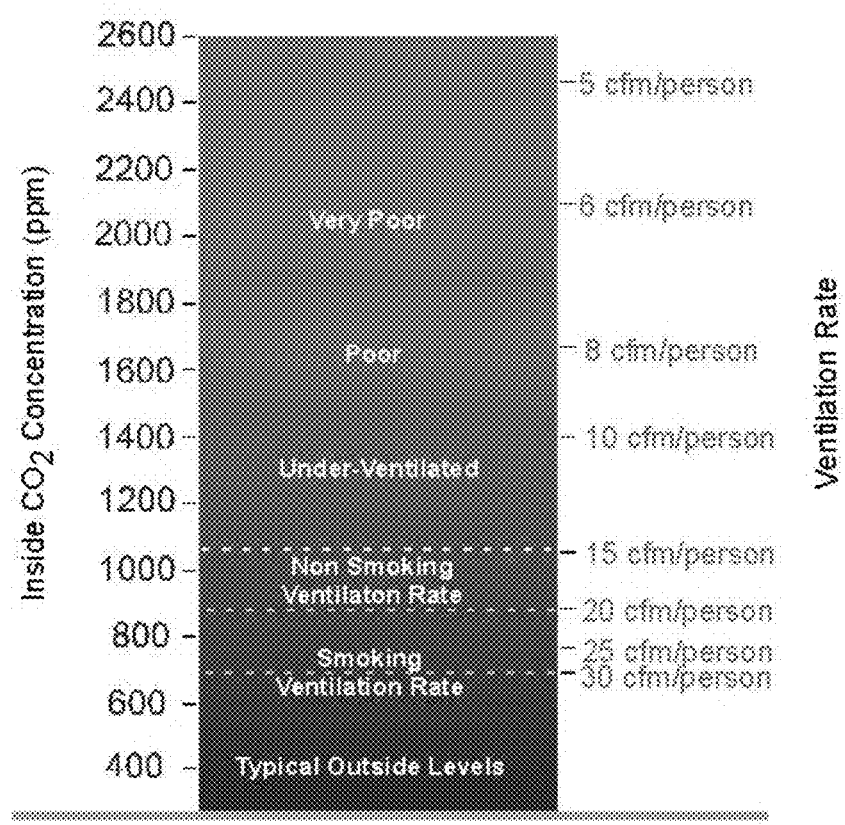

FIG. 1—schematically depicts a system for airborne viral infection risk evaluation and air quality analysis, consistent with the present inventive disclosure;

FIG. 2—presents a process for airborne viral infection risk evaluation and air quality analysis, consistent with the present inventive disclosure;

Figures 3, 4:
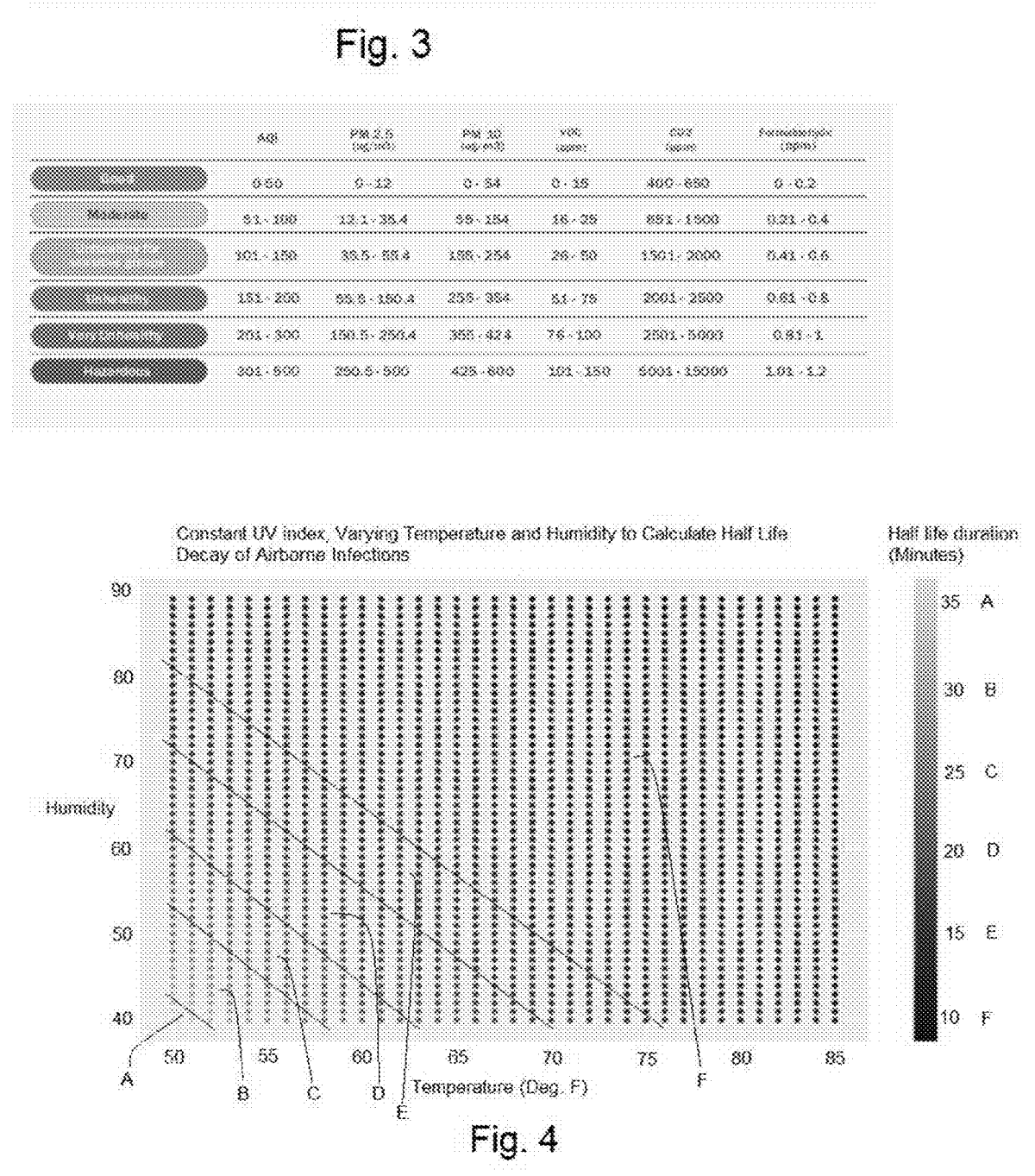

FIG. 3 is an Air Quality Index (AQI) chart, finding support in the U.S. Environmental Protection Agency Air Quality Index standards, as pertinent to the present inventive disclosure;

FIG. 4 is a 3 dimensional color plot depicting how the half-life of corona virus is related to temperature and humidity;

FIG. 5 is an example of the relationship between the recorded concentration of Fine Dust Matter (PM2.5) and how it relates to the airborne infection risk score;

FIG. 6 is a plot of viable virus percentage remaining vs time in days under various temperature and humidity conditions; and FIG. 7 presents a relationship between indoor air $CO_2$ levels and cfm-per-person of outside air ventilation rates.

Skilled artisans will appreciate that elements in the figures are generally shown schematically simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of apparatus components related to a filter apparatus. Accordingly, the apparatus components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

FIG. 1 schematically depicts a metadata driven system 100 for interacting continuously or periodically with a plurality of remotely located air quality sensors 102, 104, 106, 108 110, 112, 114 over a network, such as wide-area network 118 to receive real-time air quality measurements.

The air quality sensors, especially to support the an airborne viral infection risk calculation, may include air $CO_2$ concentration sensor 102, air fine particulate matter PM 2.5 concentration sensor 104, air inhalable particulate matter PM10 concentration sensor 106, air relative humidity sensor 108. The air quality sensors may include very fine particulate matter sensors, such as PM 2.0 PM 1.5, PM 1.0 etc., or additional types of air quality sensors.

To support the U.S. Environmental Protection Agency (EPA) standards of Air Quality Index (AQI) measurements and reports, additional sensors may include VOC volatile organic compound sensors 112, such as formaldehyde sensors 114, as well as other types of air quality sensors.

The current definition of particulate matter originated from the National Air Quality Standard for Particulate Matter (short known as PM standard) introduced in 1987 by the U.S. Environmental Protection Agency (EPA). The original definition of particulate matter was based on the 1959 Johannesburg Convention and provided for an aerodynamic diameter of 5 microns as a separating grain diameter. As an air pollutant, the airborne particulate matter has a negative effect on health, causally affecting mortality, cardiovascular diseases, cancers, respiratory diseases, and as discussed herein, is shown to effect the airborne virus transmission of the coronavirus.

PM 10 does not exactly represent a sharp division with particles of aerodynamic diameter of 10 microns; rather the PM 10 definition attempts to replicate the separation behavior of the upper respiratory tract.

PM 2.5, aerodynamic diameter of 2.5 microns, generally corresponds to "alveolene-like" particulate matter (also called fine dust). The definition is analogous to PM 10, but the weighting function is much steeper (100% weight<0.5 microns; 0% weight>3.5 microns; 50% weighting at about 2.5 microns).

As discussed earlier in the Summary section, particulate matter (PM) in the air is useful as an indicator of filtration efficiency. Increased PM levels put additional stress on the human respiratory system, and are suspected to function as virus carriers. Measurement of PM 2.5 and PM 10 concentrations are useful as a proxy to determine aerosol concentrations in the air. Carbon dioxide ($CO_2$) is directly correlated with virus concentration in the air if an infected person is in the room. Therefore $CO_2$ concentration in the air is a great indicator for indoor infection risk determination. Humidity, as discussed earlier, is important as corona virus decays more slowly in dry and in very humid environments. As discussed earlier the combination of air temperature with act humidity act together to affect the rate of virus inactivation.

The air quality sensors 102, 104, 106, 108 110, 112, 114 are arranged in one or more buildings having one or more monitored air spaces 120 (for example, room or halls, offices, school rooms, etc.). The air quality sensors 102, 104, 106, 108 110, 112, 114 communicate with the wide area network 118 to periodically or continuously transmit air quality measurement to the computer implemented airborne viral infection risk analysis and air quality calculation system 122. Preferably, the air quality sensors 102, 104, 106, 108 110, 112, 114 act autonomously to periodically push transmissions of current sensor measurements to the computer implemented airborne viral infection risk analysis and air quality calculation system 122 over the network 118. Periodic transmissions, for example, may be at 30 second, 1 minute or 5 minute intervals. Alternately, the computer implemented airborne viral infection risk analysis and air quality calculation system 122 may transmit a data request to the air quality sensors 102, 104, 106, 108 110, 112, 114, requesting a transmission of the current air quality measurements, or by reading the measurements over the network. The air quality sensors 102, 104, 106, 108 110, 112, 114 may, in some cases, operate on an exception basis, such that sensor measurements are transmitted when the sensor measurement has changed by some amount, although the exception method is not preferred.

It is preferred, but not required, that the air quality sensors 102, 104, 106, 108 110, 112, 114 are networked enabled, preferably WIFI enabled, such that they may communicate directly with the network 118 and to the computer implemented airborne viral infection risk analysis and air quality calculation system 122.

The plurality of monitored air spaces 120 are generally enclosed air spaces within buildings, such as rooms, offices, conference rooms, restaurants, stores, gather places, etc. The buildings may be separated from each other by significant distances. For example, individual buildings may be located in different states in the United States, or may be located apart in different countries, perhaps separated by oceans (for example). The wide area network 118 such as the Internet makes the location and the distance between the dispersed monitored air spaces 120 and the computer implemented airborne viral infection risk analysis and air quality calculation system 122 essentially unimportant.

The computer implemented airborne viral infection risk analysis and air quality calculation system 122 includes (shown schematically) a processor including processing circuitry 124, and a non-transitory computer-readable medium 128, the non-transitory computer-readable medium 128 containing one or more sets of computer instructions configured to instruct the processing circuitry to perform a plurality processing steps for receiving real-time air quality sensor measurements, receiving and analyzing the real-time air quality measurements of the plurality of air quality sensors and calculating an airborne viral infection risk score and the air quality indicators of one or more buildings having one or more monitored air spaces, and other process reporting and message or warning steps as discussed herein. Sensor measurement data and metadata about the measurements, analysis data or metadata from the calculating processes, generated reports, etc. may be stored to database 126. A network interface device 130 interfaces the computer implemented airborne viral infection risk analysis and air quality calculation system 122 to the wide area network 118.

The computer implemented airborne viral infection risk analysis and air quality calculation system 122 autonomously processes the received air quality sensor measurements, performs an analysis of the measurements to ultimately calculate the airborne virus airborne infection risk score, and the air quality index (AQI), generates trend reports, monthly reports, special reports on request, and provides measurement, intermediate calculated results, trends, warning and advisory e-mails and recommended action messages, and historical data to network connected devices such as smart devices, smartphones 132, tablets or computers 134 of building occupants, responsible people, owners, subscribers etc. over the network 118. As shown and well known, the smartphones 132 may communicate with the network 118 through a cellular service provider 136 having one or more cell towers 138 for wireless transmission. Computers and tablets may use this cellular link also.

As shown schematically in FIG. 1, the monitored air spaces 120 (or rooms) of buildings may optionally be provided with air treatment or filtering appliances 140 (schematically shown). The air treatment or filtering appliances 140 may be network enabled to receive control commands directly from the computer implemented airborne viral infection risk analysis and air quality calculation systems 122 over the network 118. The air treatment or filtering appliance 140 may preferably be equipped with HEPA filtering, with bio-active filter coatings and may include UV-C light treatment, to filter, capture and inactivate viruses and bacteria, and to responsively improve or correct air quality. As an alternative, the building mangers, owners, occupants, etc. may receive advisory SMS message, emails or alerts from the computer implemented airborne viral infection risk analysis and air quality calculation systems 122 over the network 118, with suggested instructions to act upon regarding room occupancy, increasing outside air flow, reducing humidity, and increasing filtration, such as through the air treatment or filtering appliance 140.

FIG. 2 presents a metadata driven computer implemented process for airborne viral infection risk evaluation and air quality analysis 200, consistent with the present inventive disclosure. The process steps described in FIG. 2 are generally intended for programmatic autonomous execution on the computer implemented airborne viral infection risk analysis and air quality calculation system 122 (see FIG. 1) with network communicated measurements from at least some of the air quality sensors 102, 104, 106, 108 110, 112, 114 and interacting over the network enabled devices 132, 134 etc. as shown in FIG. 1.

In step 202, the configured site information for dispersed buildings having monitored air spaces, customer information, etc. is read from the database 126.

Then in step 204 a building and it's one or more monitored air spaces is selected, selecting a monitored air space as the current monitored air space.

In step 206, air parameter measurements from the networked air quality sensors 102, 104, 106, 108 110, 112, 114 in the current monitored air space 120 are read over the network 118. The air parameter measurements including: air $CO_2$ concentration; air fine particulate matter PM2.5 concentration; air inhalable particulate matter PM10 concentration; air relative humidity; air temperature, and may include a fresh air flow rate sensor, if the sensor is provided, providing an measurement of volumetric fresh air flow to the monitored air space. The air parameter measurements may include volatile organic compounds (VOC), for just one example—formaldehyde concentrations, particularly for AQI calculations.

In step 208, some or all of the current air parameter measurements may optionally be smoothed by averaging together a most recent number of air parameter measurements of each sensor over a defined period of time, just for example 1 minute or 5 minutes.

In step 210, a calculated infection risk score (individually) of each measured $CO_2$, PM 2.5, PM 10, and humidity is calculated and stored to the database.

In step 212 a decay rate of viral infectivity (calculated as 1/corona virus half life) is calculated.

In step 214, the highest of the instantaneous risk score is scaled with the decay rate of viral infectivity to calculate a decay rate adjusted infection risk score.

In step 216, sensor measurements, calculations, decay rate, smoothed measurements are stored to the database, including for access by the web portal of the computer implemented airborne viral infection risk analysis and air quality calculation system 122.

In step 218, measurement data, historical trends is updated for the web portal, calculated results is updated for the web portal. SMS advisory messages are generated and sent to configured smartphones, Advisory e-mail message as generated and send to configured network devices. In some aspects of the invention, in some sites, in step 218 additional network commands or instructions may be generated and may be sent to configured network connected air treatment or filtering appliances 140 and/or building HVAC systems configured to accept network commands so as to respond proactively to improve filtration, adjust fresh air flow rates, adjust UV-C treatment, etc. to improve air quality (AQI) and reduce airborne virus risk.

In step 220, a next monitored air space of the same or a next building (is selected as the current monitored airspace. Control then transfers to step 206.

FIG. 3 is an Air Quality Index (AQI) chart, finding support in the U.S. Environmental Protection Agency Air Quality Index standards, as pertinent to the present inventive disclosure. The Air Quality Index (AQI) is determined by the worst relative pollutant concentration measured. Each category corresponds to a different level of health concern.

The Air Quality Index (AQI) was created by the U.S. Environmental Protection Agency (EPA) and is determined by the worst relative pollutant concentration measured. Each category corresponds to a different level of health concern.

FIG. 4 is a 3-dimensional color plot depicting how the half-life of corona virus is related to temperature and humidity. For better understanding in a black and white presentation, additionally the general positions of half-life duration zones are marked by letters: A=35 minutes, B=30 minutes, C=25 minutes, D=20 minutes, E=15 minutes and F=10, for a easier understanding of the plot. Black break lines are shown between the zones.

FIG. 5 is an example of the relationship between the recorded concentration of Fine Dust Matter (PM2.5) and how it relates to the airborne infection risk score. FIG. 5 is an example. Each pollutant is calculated in the same manner as this example. This relationship can be specifically defined using the following logic:

Airborne virus risk infection score=(current_pmten−pmten_low)/(pmten_high−pmten_low)

With the high and low values defined as 10 and 17 respectively (See FIG. 5).

Below 10, this value is smoothed to 0 using the following equation:

0.068*$e$^(0.5*(current_pmten/pmtwo_low*10))

FIG. 6 is a plot of the viable virus percentage remaining vs elapsed time in days.

Relative Humidity 20%, Temperature 20 C, Inactivation $\log_{10}$−0.081/day (see 602, FIG. 6)

Relevant for human to human transmission in climate in enclosed spaces, where we spend 90% of our life, work, sleeping, commuting, etc. Coronaviruses on surfaces stay viable for about a week. From these surfaces viruses may be transmitted by direct and indirect contact as well as resuspension and inhalation to susceptible persons.

(FIG. 6, 604) viable virus percentage remaining vs elapsed time in days, in heated dry indoor air (20 C 80% RH), Inactivation $\log_{10}$−0.212/day.

(FIG. 6, 606) viable virus percentage remaining vs elapsed time in days, in heated humid indoor air (20 C 50% RH). Inactivation $\log_{10}$−0.896/day.

Humidification of the air to 50% RH reduces the viable viruses to less than 1% in 2 days and significantly decreases infection risk.

Ref; Casanova L M et al. "Effects of Air Temperature and Relative Humidity on Coronavirus Survival on Surfaces", APPLIED ENVIRONMENTAL MICROBIOLOGY, May 2010 p 2712-2717.

FIG. 7 presents a relationship between indoor air $CO_2$ levels and cfm-per-person of outside air ventilation rates. This is an important factor in determining a safe occupancy rate of monitored air spaces, for example: classrooms. Increasing outdoor air ventilation can reduce the airborne concentration of SARS-CoV-2 and thus the risk of transmission through the air. In an enclosed space with low ventilation (fresh air) rate, there is a higher chance of rebreathing exhaled air and viruses. Increasing ventilation rate reduces exposure to exhaled breath and virus containing aerosols or airborne viruses. As a result the $CO_2$ concentration in an indoor space can be directly related to a fresh air ventilation rate per-person in the space, therefore it directly correlates with virus concentration in the air. FIG. 7 shows a relationship between $CO_2$ levels and cfm-per-person outside fresh air ventilation rates. For each ventilation rate there is a corresponding $CO_2$ level. Assuming an outside concentration of 400 ppm, an indoor $CO_2$ concentration of 1100 ppm would be considered equivalent to 15 cfm per person and a concentration of 700 ppm would be considered equivalent to 30 cfm/person. The correlation of $CO_2$ levels to fresh air ventilation rates is independent of the number of occupants in the room.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

What is claimed is:

1. A metadata driven computer implemented process of interacting continuously or periodically with a plurality of remotely located air quality sensors over a network to receive real-time air quality measurements, receiving and analyzing the real-time air quality measurements of a plurality of air quality sensors and calculating an airborne viral infection risk score and air quality indicators of one or more buildings having one or more monitored air spaces, the computer implemented process comprising:
   a local or wide area network communications interface device, configured to communicate over a network with the plurality of remote air quality sensors measuring air quality parameters within the monitored air spaces of the one or more buildings;
   a database for storing current and history data;
   a network web portal configured to provide remote network access and presentation of measurements, analysis results and reports over the network to remote network connected devices;
   processing circuitry, and a non-transitory computer-readable medium, the non-transitory computer-readable medium containing one or more sets of computer instructions configured to instruct the processing circuitry to perform a plurality process steps including:
      communicating with the plurality of air quality sensors and retrieving over the network current indoor air quality measurements of the monitored air space in the one or more buildings, the air parameter measurements including:
         air $CO_2$ concentration;
         air fine particulate matter PM2.5 concentration;
         air inhalable particulate matter PM10 concentration;
         air relative humidity; and
         air temperature;
      adding a time-date stamp and storing the current sensor air parameter measurements and storing to the database;
      smoothing the sensor air parameter measurements by averaging the current sensor air parameter measurements with the previous air parameter measurements of the same sensor over a configured period of time, the smoothing to reduce measurement noise;
      storing the smoothed sensor air parameter measurements to the database for access by the web portal;
      calculating a $CO_2$ instantaneous airborne infection risk score from the smoothed $CO_2$ sensor air parameter measurement of the monitored air space;
      calculating a PM2.5 instantaneous airborne infection risk score from the smoothed PM2.5 sensor air parameter measurement of the monitored air space;
      calculating a PM10 instantaneous airborne infection risk score from the smoothed PM10 sensor air parameter measurement of the monitored air space;
      calculating relative humidity instantaneous airborne infection risk score from the smoothed relative humidity sensor air parameter measurement of the monitored air space;
      storing the instantaneous airborne infection risk scores to the database for access by the web portal;
      determining which one of measurement types $CO_2$, PM2.5, PM10 and relative humidity have a highest instantaneous airborne virus infection risk score;
      calculating a decay rate for viral infectivity as a function of the smoothed air temperature and smoothed relative humidity of the monitored air space,
      wherein the decay rate for viral infectivity is 1/(a calculated virus half-life);
      applying the decay rate for viral infectivity as a scale factor to the highest instantaneous airborne infection risk score to obtain an overall decay rate adjusted highest instantaneous airborne virus infection risk score;
      storing the overall decay rate adjusted highest instantaneous airborne virus infection risk score and the highest measurement type to the database for access by the web portal;
      repeating the plurality process steps for a next or same monitored air space.

2. The computer implemented process according to claim 1, wherein
   after the step of applying the decay rate for viral infectivity as a scale factor, the method further includes:
      communicating the overall decay rate adjusted highest instantaneous airborne virus infection risk score over the network to network connected smartphones, tablets or network connected devices configured to receive air quality or infection risk updates.

3. The computer implemented process according to claim 2, wherein
   the step of communicating the overall decay rate adjusted highest instantaneous airborne virus infection risk score further includes the steps of:
      reading configured risk level thresholds from the database;
      if the highest instantaneous airborne virus infection risk score is >=the configured risk level threshold, then transmitting a warning message to network connected smartphones, tablets or network connected devices configured to receive infection risk updates.

4. The computer implemented process according to claim 1, wherein
   in the step of communicating with the plurality of air quality sensors, the air quality sensor air parameter measurements further include:
      an air volatile organic compound (VOC) concentration, selected from the set consisting of formaldehyde, toluene and xylenes, or combinations thereof;
   wherein after the step of adding a time-date stamp and storing the current sensor air parameter measurements and storing to the database, the method further comprises:

calculating an Air Quality Index (AQI) from the smoothed sensor air parameter measurements of the monitored air space; and storing the Air Quality Index (AQI) to the database for access by the web portal.

5. The computer implemented process according to claim 2, wherein after the step of applying the decay rate for viral infectivity as a scale factor, the method further includes:

generating e-mail and/or SMS risk score notification messages and transmitting over the network or a cellular network to smartphones, tablets or network connected devices configured to notifications for the current monitored air space.

* * * * *